United States Patent
Conrad

(10) Patent No.: US 10,314,691 B2
(45) Date of Patent: Jun. 11, 2019

(54) INTRA-OCULAR DEVICE

(71) Applicant: Verily Life Sciences LLC, Mountain View, CA (US)

(72) Inventor: Andrew Jason Conrad, Malibu, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/522,710

(22) Filed: Oct. 24, 2014

(65) Prior Publication Data

US 2016/0113760 A1    Apr. 28, 2016

(51) Int. Cl.
*A61F 2/16* (2006.01)
(52) U.S. Cl.
CPC .......... *A61F 2/1627* (2013.01); *A61F 2/1648* (2013.01); *A61F 2002/1682* (2015.04); *A61F 2002/16901* (2015.04); *A61F 2250/0001* (2013.01)
(58) Field of Classification Search
CPC .................................................... A61F 2/1624
See application file for complete search history.

(56) References Cited

U.S. PATENT DOCUMENTS

| | | |
|---|---|---|
| 5,171,266 A | 12/1992 | Wiley et al. |
| 5,476,515 A | 12/1995 | Kelman et al. |
| 6,702,853 B1 * | 3/2004 | Peyman ................ A61F 2/1602 623/6.12 |
| 8,574,295 B2 | 11/2013 | Roholt |
| 8,721,074 B2 | 5/2014 | Pugh et al. |
| 8,827,446 B2 | 9/2014 | Iyer et al. |
| 2006/0095128 A1 * | 5/2006 | Blum ........................ A61F 2/16 623/6.37 |

(Continued)

FOREIGN PATENT DOCUMENTS

| | | |
|---|---|---|
| WO | 2006/050171 A2 | 5/2006 |
| WO | 2012122411 A1 | 9/2012 |

OTHER PUBLICATIONS

International Search Report and Written Opinion of International Application No. PCT/US2015/056855 dated Jan. 21, 2016 (dated Jan. 21, 2016).

(Continued)

*Primary Examiner* — Leslie Lopez
(74) *Attorney, Agent, or Firm* — McDonnell Boehnen Hulbert & Berghoff LLP

(57) ABSTRACT

An intra-ocular device includes an electronic lens that can be controlled to control the overall optical power of the device. The device can be installed within a flexible polymeric material shaped to conform to the inside surface of a lens capsule of an eye. Accommodation forces applied to the device and/or polymeric material via the lens capsule can cause a change in the optical power of the device and/or polymeric material. Further, such accommodation forces can be detected by an accommodation sensor of the device and the optical power of the electronic lens can be controlled based on the detected accommodation forces. Operated in this way, the device and polymeric material can restore a degree of accommodation to the eye that is related to existing mechanisms for controlling such accommodation, i.e., forces exerted by the eye via the lens capsule.

11 Claims, 7 Drawing Sheets

(56) References Cited

U.S. PATENT DOCUMENTS

| | | |
|---|---|---|
| 2006/0206205 A1 | 9/2006 | Azar |
| 2010/0072643 A1* | 3/2010 | Pugh ................ B29D 11/00038 |
| | | 264/2.7 |
| 2012/0019773 A1 | 1/2012 | Blum et al. |
| 2012/0236524 A1* | 9/2012 | Pugh ........................ G02C 7/04 |
| | | 361/783 |
| 2013/0083405 A1* | 4/2013 | Trajkovska ............ H01B 1/124 |
| | | 359/642 |
| 2013/0245754 A1* | 9/2013 | Blum .................... A61F 2/1627 |
| | | 623/6.13 |
| 2013/0338767 A1 | 12/2013 | Mazzocchi et al. |
| 2014/0156000 A1 | 6/2014 | Campin et al. |
| 2014/0240665 A1 | 8/2014 | Pugh et al. |
| 2014/0277291 A1* | 9/2014 | Pugh ........................ G02C 7/04 |
| | | 607/88 |

OTHER PUBLICATIONS

European Search Report, European Patent Application No. 15852556, dated Mar. 19, 2018, 10 pages.

\* cited by examiner

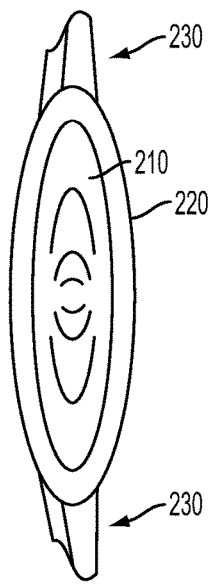 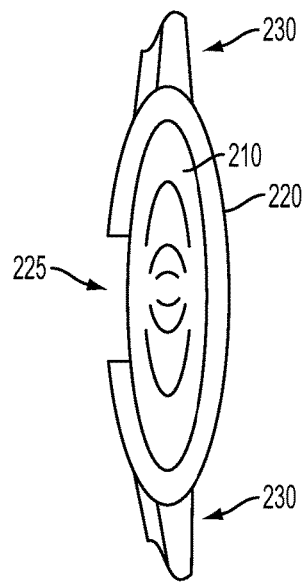 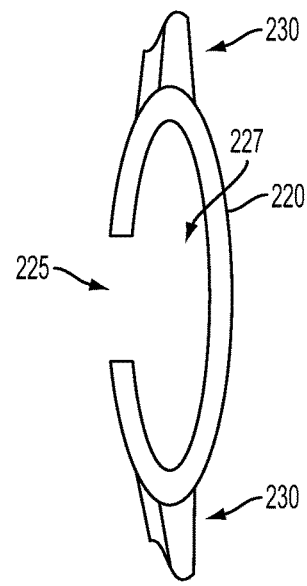
FIG. 2A  FIG. 2B  FIG. 2C
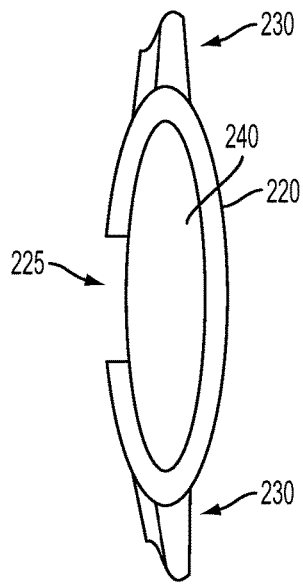 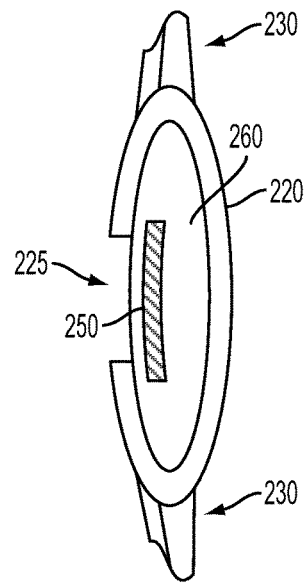
FIG. 2D  FIG. 2E

FIG. 5DFIG. 5E

INTRA-OCULAR DEVICE

BACKGROUND

Unless otherwise indicated herein, the materials described in this section are not prior art to the claims in this application and are not admitted to be prior art by inclusion in this section.

Elements of the human eye (e.g., the cornea, lens, aqueous and vitreous humor) operate to image the environment of the eye by focusing light from the environment onto the retina of the eye, such that images of elements of the environment are presented in-focus on the retina. The optical power of the natural lens of the eye can be controlled (e.g., by ciliary muscles of the eye) to allow objects at different distances to be in focus at different points in time (a process known as accommodation).

A variety of congenital, acquired, and/or degenerative disease states of the eye result in decreased focus, decreased accommodation, or other degradation of images presented to the retina. For example, presbyopia, a decrease in the ability of the eye to accommodate the crystalline lens, develops in most individuals as their age increases. Issues with poor focus can be rectified by the use of eyeglasses and/or contact lenses or by the remodeling of the cornea. Further, artificial lenses can be implanted into the eye (e.g., into the space in front of the iris, into the lens capsule following partial or full removal of the natural lens, e.g., due to the development of cataracts) to improve vision.

SUMMARY

Some embodiments of the present disclosure provide a method including: (i) injecting a fluid into a lens capsule of an eye, wherein a natural lens of the eye has been removed from the lens capsule; (ii) positioning an intra-ocular device within the fluid in the lens capsule, wherein the intra-ocular device includes an electronic lens, wherein the electronic lens can be controlled to provide an optical power within a range of optical powers, and wherein the optical power of the electronic lens is controlled in part by an electrical signal applied to the electronic lens; and (iii) solidifying the fluid in the lens capsule to form a coupling between the lens capsule and the intra-ocular device, such that accommodation forces can be applied to the intra-ocular device via the lens capsule and coupling.

Some embodiments of the present disclosure provide an intra-ocular device, including: (i) an electronic lens, wherein the electronic lens can be controlled to provide an optical power within a range of optical powers, and wherein the optical power of the electronic lens is controlled in part by an electrical signal applied to the electronic lens; (ii) an accommodation sensor, wherein the accommodation sensor is configured to detect accommodation forces applied to the intra-ocular device via a lens capsule of an eye when the intra-ocular lens is disposed in the lens capsule; and (iii) a controller, wherein the controller is operatively coupled to the electronic lens and the accommodation sensor, wherein the controller is configured to apply an electrical signal to the electronic lens to control the optical power of the electronic lens based on the accommodation forces detected by the accommodation sensor.

Some embodiments of the present disclosure provide a method including: (i) detecting, by an accommodation sensor of an intra-ocular device, accommodation forces applied to the intra-ocular device via a lens capsule of an eye, wherein the intra-ocular device is disposed within the lens capsule, wherein the intra-ocular device further includes: (1) an electronic lens, wherein the electronic lens can be controlled to provide an optical power within a range of optical powers, and wherein the optical power of the electronic lens is controlled in part by an electrical signal applied to the electronic lens; (2) a controller, wherein the controller is operatively coupled to the electronic lens and the accommodation sensor; and (ii) controlling, using the controller, the optical power of the electronic lens based on the detected accommodation forces, wherein controlling the optical power of the electronic lens includes applying an electrical signal to the electronic lens.

Some embodiments of the present disclosure provide an intra-ocular device, including: (i) electronic lensing means, wherein the electronic lensing means can be controlled to provide an optical power within a range of optical powers, and wherein the optical power of the electronic lensing means is controlled in part by an electrical signal applied to the electronic lensing means; (ii) accommodation sensing means, wherein the accommodation sensing means are configured to detect accommodation forces applied to the intra-ocular device via a lens capsule of an eye when the intra-ocular lens is disposed in the lens capsule; and (iii) controller means, wherein the controller means are operatively coupled to the electronic lensing means and the accommodation sensing means, wherein the controller means are configured to apply an electrical signal to the electronic lensing means to control the optical power of the electronic lensing means based on the accommodation forces detected by the accommodation sensing means.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is a side cross-section view of a natural lens in a lens capsule of an eye.

FIG. 2B is a side-cross section view of the natural lens and lens capsule of FIG. 2A after an aperture has been made in the lens capsule.

FIG. 2C is a side-cross section view of the lens capsule of FIG. 2B after the natural lens has been removed.

FIG. 2D is a side-cross section view of the lens capsule of FIG. 2C after a fluid has been introduced into the lens capsule.

FIG. 2E is a side-cross section view of the lens capsule of FIG. 2D after an intra-ocular device has been introduced into the lens capsule.

FIG. 5D is a top view of the example intra-ocular device of FIG. 5A embedded within a polymeric material.

FIG. 5E is side cross-section view of the example intra-ocular device embedded within the polymeric material shown in FIG. 5D.

DETAILED DESCRIPTION

Figure 1A:
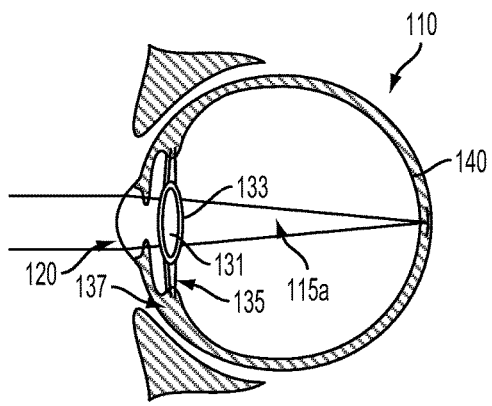
FIG. 1A is a side cross-section view of a human eye when the eye is focusing on a distant object.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

An intra-ocular device could be positioned within a lens capsule of an eye (following the removal of the natural lens from the lens capsule) to provide a means for focusing light from outside the eye onto the retina of the eye. Such an intra-ocular device could include an electronic lens that can be controlled to provide an optical power (e.g., a degree of focusing of light, such as may be measured in diopters) within a range of optical powers. The optical power of the electronic lens could be controlled to focus images of near and far objects alternatively over time. That is, the electronic lens could be controlled to have a first optical power during a first period of time to provide images of far objects (e.g., objects more than approximately 20 centimeters away from the eye) in focus on the retina of the eye, and the electronic lens could be controlled to have a second optical power greater than the first optical power during a second period of time to provide images of near objects (e.g., objects approximately 9 centimeters away from the eye) in focus on the retina of the eye.

Control of the optical power of the electronic lens could be related to accommodation forces applied to the intra-ocular device via the lens capsule. Such accommodation forces could be coupled to the intra-ocular device by a polymeric material configured to be in contact with the inside surface of the lens capsule. The intra-ocular device could be disposed within the polymeric material such that accommodation forces applied to the polymeric material (via the lens capsule) can be coupled to the intra-ocular device. The polymeric material could be configured to maintain the shape, volume, and/or structural integrity of the lens capsule after installation (e.g., after the formation of a rhexis (i.e., tear) in the lens capsule to allow removal of a natural lens and installation of the intra-ocular device and polymeric material). The optical power of the electronic lens could be controlled by the coupled accommodation forces directly (e.g., the coupled accommodation forces could deform the electronic lens or other elements of the intra-ocular device and/or polymeric material, causing a change in the optical power thereof) and/or indirectly (e.g., the coupled accommodation forces could be detected by an accommodation sensor of the intra-ocular device and the electronic lens could be electronically controlled based on the detected accommodation force). In examples wherein accommodation forces at least partially directly control the optical power of the intra-ocular device, a power requirement of the intra-ocular device could be reduced relative to examples wherein controlling the optical power of the intra-ocular device is effected primarily by active electronic control of the electronic lens.

Coupling of forces between the intra-ocular device and the lens capsule could be achieved by forming and/or disposing a polymeric or other flexible, deformable material around the intra-ocular device and in contact with the inner surface of the lens capsule. Such a material formed and/or disposed to be in contact with the lens capsule could couple forces from the lens capsule, through deformation of the material, to the intra-ocular device. Such coupled forces could act to deform all (i.e., the intra-ocular device could be wholly flexible) or part (i.e., the intra-ocular device could include one or more rigid elements) of the intra-ocular device. Such deformations could cause a change in the optical power of one or more optical elements of the intra-ocular device (e.g., by changing a geometry or a flexible electronic lens and/or some other type of flexible lens) and/or could be detected by the intra-ocular device (e.g., by an accommodation sensor) and used by electronics of the intra-ocular device to control the optical power of an electronic lens of the intra-ocular device.

Such a force-coupling material could be formed by depositing a fluid into the lens capsule (following removal of the lens from the lens capsule), positioning the intra-ocular device within the fluid in the lens capsule (e.g., aligned with an optical axis of the eye), and solidifying the fluid (e.g., by photopolymerization or some other process related to the composition of the fluid). A material formed through such a process could be in intimate contact with the inner surface of the lens capsule, allowing coupling of forces from the lens capsule into the polymeric material and further into any contents of the material (e.g., into the intra-ocular device). Positioning of the intra-ocular device, fluid, material, or other elements could be accomplished by using a laser or other surgical instrument to form a hole in the anterior surface of the lens capsule. The existing natural lens could be removed by fragmentation (e.g., using ultrasonic vibrations) and removed (e.g., via suction in concert with a matched addition of fluids to maintain the volume and shape of the lens capsule).

The electronic lens could be configured in a variety of ways to enable electronic control of the optical power of the electronic lens. The electronic lens could include piezo elements, electro-wetting elements, liquid crystal elements and/or reservoirs, microfluidic elements and/or reservoirs, or other electronic actuators configured to change a geometry (e.g., a shape, a thickness, a curvature) of the electronic lens based on an electric signal applied to the electronic lens. Additionally or alternatively, an optical property (e.g., an index of refraction, a degree and/or direction of birefringence, a degree and/or spectrum of reflectivity and/or opacity) of one or more elements of the electronic lens could be controlled based on an electrical signal applied to the electronic lens. For example, the electronic lens could include a layer of liquid crystal (e.g., nematic liquid crystal)

disposed between two substantially transparent conductors such that, when an oscillating voltage signal is applied across the conductors, an effective refractive index of the liquid crystal is changed based on one or more properties of the applied oscillating voltage signal. Such a liquid crystal and associated transparent conductors could be flexible (e.g., the conductors could be a plurality of silver nanowires) to enable deformation of the electronic lens and/or the intra-ocular device by accommodation forces applied via the lens capsule.

Further, such an intra-ocular device could include one or more additional lenses (e.g., flexible silicone elastomer lenses) configured to provide additional optical power to the intra-ocular device in combination with the electronic lens. The optical power and other properties of the additional lens(es) and electronic lens could be specified relative to properties of the eye (e.g., a geometry of the eye and/or of the retina and cornea of the eye) to provide correction for myopia, hyperopia, astigmatism, or some other optical defect or aberration of the eye. In some examples, an unpowered state of the intra-ocular device (i.e., a state wherein the intra-ocular device is not receiving external power and/or a battery of the intra-ocular device is discharged) could provide an optical power such that far objects can be imaged in-focus by the user's eye.

Such an intra-ocular device could include a controller or other electronic elements configured to operate the electronic lens and accommodation sensor of the intra-ocular device. Such a controller could be configured to detect a deformation, stress, strain, curvature, pressure, or other information or property related to accommodation forces applied via the lens capsule and the coupling material using the accommodation sensor. The controller could further apply an electrical signal (e.g., a DC voltage, an oscillating electrical signal) to the electronic lens to control the optical power of the electronic lens based on the detected accommodation forces. This could include applying the electrical signal based on calibration data (e.g., data relating detected outputs of the accommodation sensor to electrical signals applied to the electronic lens) stored in a data storage of the intra-ocular device (e.g., in flash and/or EEPROM memory of the controller). The controller, other elements of the intra-ocular device (e.g., antennas, batteries), interconnects between the elements of the intra-ocular device, electronic lens, and/or accommodation sensor could be flexible, e.g., could be composed of flexible conductors, flexible semiconductors, or other flexible materials or components.

The intra-ocular device could include other elements. In some examples, the intra-ocular device could include one or more antennas configured to enable communication with an external system and/or reception of wireless power by the intra-ocular device. For example, the intra-ocular device could be powered by receiving power from an external wireless power emitter (e.g., a wireless power emitter disposed in a pair of eyeglasses or some other device worn by a user of the intra-ocular device). Additionally or alternatively, the intra-ocular device could include a battery (e.g., a solid-state, thin-film battery) and could be powered by the battery. In some examples, the battery could be recharged by wireless power received by the antenna (e.g., the intra-ocular device could be powered by the battery during the day, and could be recharged by wireless power received using an antenna of the intra-ocular device during the night, e.g., from a wireless power transmitter disposed near a bed of a user of the intra-ocular device). An antenna could be used to transmit information to an external system (e.g., to transmit detected accommodation forces, e.g., for use as part of human interface system) and/or to receive information from an external system (e.g., to receive updated calibration data relating detected accommodation forces to applied electrical signals). Such communications could be encrypted.

Other configurations, modes and methods of operation, and other embodiments are anticipated. Systems and/or methods described herein could include additional optical elements, methods of detecting accommodation and/or otherwise detecting a desired lens optical power, electronic lenses, or other elements to provide additional functionality according to an application. A system as described herein could be formed and/or emplaced in a lens capsule or other region and/or tissue of an eye according to an application. Systems as described herein could be applied toward restoring and/or enhancing vision of a human or animal or toward some other application. Other applications, operations, and configurations of electronic optical devices as described herein are anticipated.

It should be understood that the above embodiments, and other embodiments described herein, are provided for explanatory purposes, and are not intended to be limiting.

Further, the term "lens capsule" as used herein should be understood broadly to include tissues of the eye that, under normal biological conditions, contain the natural lens (i.e., the crystalline lens) and that transmit forces into the natural lens to at least partially control the shape of the natural lens. "Lens capsule" could refer to the natural, intact lens capsule, a lens capsule that has been penetrated or otherwise surgically altered, and/or a lens capsule that has had some aspect (e.g., a portion of the anterior surface of the lens capsule) surgically or otherwise removed. The term "accommodation forces" is intended to refer to forces applied to contents of the lens capsule both by the tissues of the lens capsule itself (e.g., due to the geometry, elasticity, and other properties of the tissues of the capsule) and by external tissue acting on/through the lens capsule (e.g., forces applied by the ciliary muscles through the zonules).

II. ACCOMMODATION OF THE EYE THROUGH NATURAL AND ARTIFICIAL PROCESSES

Generally, human (and animal) eyes include a variety of elements configured to focus or otherwise manipulate light from the environment of the human such that the light can be detected in focus on a retina of the eye and used to image the environment. In particular, a human eye includes refractive lensing elements (e.g., a crystalline lens, a cornea), a controllable aperture (e.g., an iris), and a light-sensitive element (e.g., the retina).

Objects located at different locations in the environment (e.g., different distances from the eye) could be imaged by controlling one or more elements of the eye to focus light from a particular object onto the retina. That is, the eye could be controlled to have a first optical power (e.g., measured in diopters) during a first period of time to allow objects at a first distance from the eye to be imaged in-focus by the retina. The eye could be controlled, during a second period of time, to have a second optical power higher than the first optical power to allow objects at a second distance that is closer than the first distance to be imaged in-focus. This process of controlling the optical power of the eye (by controlling properties of one or more elements of the eye) over time to allow in-focus imaging of objects at different distances over time is referred to herein as accommodation.

The overall optical power of an eye is provided by a combination of the optical power of a number of elements of the eye. The majority of the optical power of a human eye is provided by the curved interface between the lower index-of-refraction air in front of the eye and the higher index-of-refraction cornea and aqueous humor of the front aspects of the eye. The curved geometry and non-uniform, higher-than-surrounding-tissues index-of-refraction of the crystalline lens of the eye provides further optical power to the eye. Accommodation in the human eye (i.e., controlling of the overall optical power of the eye to allow for in-focus imaging of objects at different distances from the eye during different periods of time, as described above) is generally achieved by operating one or more elements of the eye (e.g., the ciliary muscle(s)) to change the geometry of the crystalline lens, thus changing the optical power of the crystalline lens.

To illustrate the configuration and operation of the human eye to image objects in an environment, FIG. 1A shows a cross-section view through the center of an eye 110. The eye 110 includes a cornea 120, crystalline lens 131, and other elements configured to focus light from the environment, by refraction, onto a retina 140 of the eye. The crystalline lens 131 is located within a lens capsule 133 that is connected via zonules 135 to the ciliary body 137 of the eye 110. As shown in FIG. 1A, elements of the eye 110 are configured such that far object light 115a (i.e., light reflected, emitted, or otherwise received by the eye 110 from a distant object) is refracted by the cornea 120, crystalline lens 131, and other elements of the eye 110 such the far object light 115a is in-focus at the retina 140. Thus, the corresponding distant object can be imaged, in-focus, by the eye 110.

Imaging an object in-focus generally means refracting, reflecting, diffracting, filtering, or otherwise optically manipulating light from the object such that substantially all of the light received from a particular point (or other small region of the object) is detected at a single light-sensitive point (or other small constrained region) of an imager (e.g., by one or more light-sensitive cells located in a small region of the retina 140 of the eye 110). As shown in FIG. 1A, light from such a particular point of a distance object can be substantially parallel at the eye 110. In contrast, light from nearer objects can be more divergent and/or exhibit a greater range of angles at the eye 110, requiring the eye 110 to have a greater effective optical power in order to bring the light from the nearer object into focus at the retina 140.

Figure 1B:
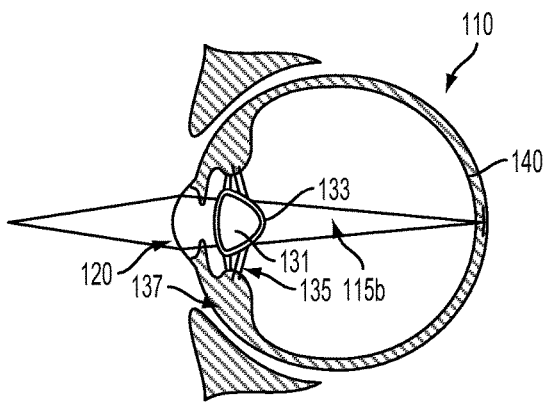
FIG. 1B is a side cross-section view of the human eye of FIG. 1A when the eye is focusing on a near object.

As an illustrative example, FIG. 1B shows a cross-section view through the center of the eye 110 illustrated in FIG. 1A during a second period of time. As shown in FIG. 1B, elements of the eye 110 are configured such that near object light 115b (i.e., light reflected, emitted, or otherwise received by the eye 110 from a near object) is refracted by the cornea 120, crystalline lens 131, and other elements of the eye 110 such the near object light 115b is in-focus at the retina 140. Thus, the corresponding near object can be imaged, in-focus, by the eye 110.

Generally, changes in the overall optical power of the eye related to accommodation are caused by changes of the optical power of the crystalline lens 131. That is, accommodation is effected primarily by controlling the shape of the crystalline lens 131 and thus controlling the optical power of the crystalline lens 131. For example, the crystalline lens 131 in FIG. 1A is flattened, while the crystalline lens 131 is thicker and rounder in FIG. 1B. Such changes in shape of the crystalline lens 131 can be caused be forces applied to the crystalline lens 131 by the lens capsule 133. Such forces can be due in part to the shape and structure of the lens capsule, e.g., forces applied to the crystalline lens 131 due to the elasticity of the lens capsule 133. That is, if the zonules 135 were severed, the crystalline lens 131 and lens capsule 133 would assume a thickened, round shape. Forces applied to the lens capsule 133 and to the crystalline lens 131 via the lens capsule 133 also affect the shape of the crystalline lens 131. Contraction and/or relaxation of muscle fibers in the ring of tissue comprising the ciliary body 137 can cause changes in forces applied to the lens capsule 133 by the zonules 135 such that the overall shape and optical power of the crystalline lens 131 can be controlled by contracting and/or relaxing muscle fibers of the ciliary body 137. Such contraction and/or relaxation of ciliary body 137 muscle fibers is controlled by the central nervous system to focus on target objects in the environment of the eye. Such operation of the ciliary body is often accompanies by other physiological and/or nervous changes, for example, contraction/dilation of the iris of the eye and convergence of the eyes.

In some situations, the ability of the eye to accommodate to focus on objects at different distances can be reduced or lost. Presbyopia is an age-related condition wherein the ability of the eye to accommodate (i.e., to change focus in order to image objects at different distances) decreases with increasing age. The development of presbyopia could be related to an increased stiffness of the crystalline lens of the eye, a decreased strength of the ciliary muscles or other muscles of the eye whose relaxation and/or contraction are related to accommodation, or to other conditions or properties of the eye.

A flexible device could be installed in the lens capsule after removal of the natural lens and configured to have an optical power that is related to accommodation forces (i.e., forces applied by and/or through the lens capsule) applied to the flexible device. Such changes in optical power could be due in part due to changes in the geometry of the device (e.g., deformation of the device) caused by the accommodation forces and/or partially due to operation of one or more electronic optical elements (e.g., an electronic lens) based on the accommodation forces as measured by one or more sensors.

Figure 1C:
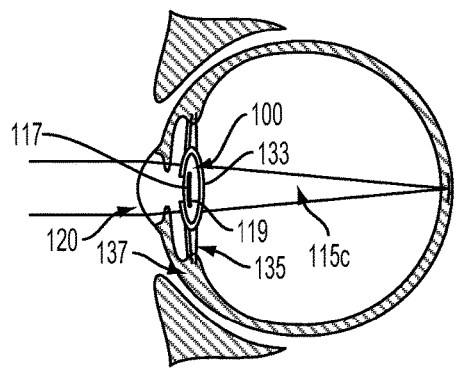
FIG. 1C is a side cross-section view of a human eye containing an intra-ocular device when the eye and intra-ocular device are focusing on a distant object.

As an example, FIG. 1C shows the eye 110 of FIGS. 1A and 1B after the natural lens 131 has been removed from the lens capsule 133 and replaced with an intra-ocular device 100. The intra-ocular device 100 includes an active element 117 disposed within a flexible polymeric material 119. The polymeric material 119 is configured to couple accommodation forces from the lens capsule 133 to the active element 117. As shown in FIG. 1C, elements of the eye 110 and the intra-ocular device 100 are configured such that far object light 115c (i.e., light reflected, emitted, or otherwise received by the eye 110 from a distant object) is refracted by the cornea 120, intra-ocular device 100 (e.g., 117, 119), and other elements of the eye 110 such the far object light 115c is in-focus at the retina 140. Thus, the corresponding distant object can be imaged, in-focus, by the eye 110.

Accommodation forces (e.g., forces applied to the polymeric material by and/or through the lens capsule 133) could cause a change in the overall optical power of the eye 110, allowing partial or complete restoration of the ability of the eye 110 to accommodate (i.e., to focus during different periods of time on objects at different distances from the eye by activity of the elements of the eye 110 (e.g., contraction and/or relaxation of muscle fibers of the ciliary body 137)). This could include the accommodation forces changing an optical power of the polymeric material 119 and/or active element 117 by changing a geometry (e.g., deforming) the polymeric material 119 and/or active element 117. Additionally or alternatively, the accommodation force could be detected by the active element 117 (e.g., by an accommodation sensor of the active element 117) and the optical power of one or more elements of the active element 117 could be controlled based on the detected accommodation force.

Figure 1D:
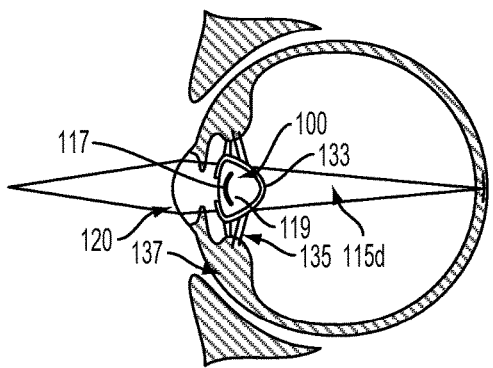
FIG. 1D is a side cross-section view of the human eye containing the intra-ocular device of FIG. 1C when the eye and intra-ocular device are focusing on a near object.

As an illustrative example, FIG. 1D shows a cross-section view through the center of the eye 110 illustrated in FIG. 1D during a second period of time. As shown in FIG. 1D, elements of the eye 110 and intra-ocular device 100 are configured such that near object light 115*d* (i.e., light reflected, emitted, or otherwise received by the eye 110 from a near object) is refracted by the cornea 120, intra-ocular device 100 (e.g., 117, 119), and other elements of the eye 110 such the near object light 115*d* is in-focus at the retina 140. Thus, the corresponding near object can be imaged, in-focus, by the eye 110.

The polymeric material 119 could have a refractive index that is different than the refractive index of surrounding materials (e.g., aqueous humor, vitreous humor) such that light passing through the polymeric material 119 is refracted. The optical power of such a polymeric material 119 could be related to the difference between the refractive index of the polymeric material 119 and the refractive index of surrounding materials and to the geometry of the polymeric material. Thus, changes in the geometry of the polymeric material 119 (e.g., in response to the application of accommodation forces to the polymeric material 119, as shown in FIGS. 1C and 1D) could result in changes in the optical power of the polymeric material. Alternatively, the refractive index of the polymeric material 119 could be substantially the same as the refractive index of surrounding materials, such that the optical power of the polymeric material 119 is substantially zero.

The polymeric material 119 could be composed of one or more of a variety of materials. The polymeric material 119 could include a silicone hydrogel. One or more properties of the contents of the polymeric material 119 (e.g., a ratio of monomers or other chemicals used to form the polymeric material 119) could be specified such that a refractive index or other properties of the polymeric material 119 are specified according to an application. In some examples, the polymeric material 119 could be formed such that a refractive index of the polymeric material 119 was non-uniform (e.g., such that the polymeric material 119 formed a gradient-index lens).

As shown in FIGS. 1C and 1D, accommodation forces coupled to the active device 117 cause a deformation of the active device 117. Such a deformation could cause a change in the optical power of the active device 117 directly (by changing the geometry of one or more refractive elements, e.g., silicone hydrogel lenses, electronic liquid-crystal lenses, by affecting a valve, pump, or other microfluidic element(s)). Such a deformation could cause a change in the optical power of the active device 117 indirectly. For example, an accommodation sensor (e.g., a strain sensor, a stress sensor, a flex sensor, a pressure sensor) could detect a deformation (or some property of the active device 117 related to the deformation, e.g., a stress, a strain, a pressure, a curvature) and the optical power of an element (e.g., an electronic lens) of the active device 117 could be controlled based on the output of the accommodation sensor. As shown in FIGS. 1C and 1D, accommodation forces coupled to the active device 117 can cause deformation of the entire active device 117. However, in other embodiments, one or more parts of an active device could be rigid. For example, a central portion of an active device (containing, e.g., one or more fixed-power lenses, one or more controlled-power electronic lenses, other electronics) could be rigid, while peripheral portion(s) of the active device could be deformable and could include one or more accommodation sensors such that accommodation forces coupled to the active device by a polymeric material could be detected and used to operate the active device (e.g., to control an optical power of an electronic lens of the active device). Multiple fixed and/or controllable lens components of the active device 117 could be configured to provide an overall optical power of the active device 117 in combination with each other (e.g., an additional lens of the active device 117 could be configured to provide an additional optical power in combination with the optical power of the electronic lens of the active device 117). Other configurations of wholly and/or partially flexible active elements or other components of an intra-ocular device (e.g., 100) are anticipated.

The optical power of the active device 117 could be controlled based on other properties/factors. For example, the active device 117 could include one or more light sensors, and the active device 117 could be configured to control the optical power of one or more electronic lenses of the active device 117 based on the output of the one or more light sensors, and/or based on a combination of the output of the one or more light sensors and the output of an accommodation sensor of the active device 117. The active device 117 could be configured to receive an input from a control device (e.g., by including an antenna, light sensor, or other element configured to receive transmitted commands from such a control device). A user could operate such a control device to set an optical power of the active device based on user preferences (e.g., to increase the optical power of the active device 117 when the user is attempting to focus on a near object, e.g., to read a book held near the eyes of the user). User commands and detected accommodation forces during such operation could be used to update calibration data or other information describing the operation of the active device 117 (e.g., to develop a correspondence between detected accommodation forces, as generated by the eye 110 of the user, and controlled optical powers of the active device 117 according to the preferences of the user).

Elements of the intra-ocular device 100 could be configured according to additional or alternative applications. In some examples, elements of the active device 117 and/or polymeric material 119 could be configured to block harmful light from reaching the retina 140 (e.g., to block light below a specified wavelength, to block ultraviolet light). One or more elements of the active device 117 could be configured to provide an optical power or other optical effect to provide correction for myopia, hyperopia, astigmatism, or other properties of the eye 110. Additionally or alternatively, one or more flexible or rigid lenses (not shown) could be provided on or within the polymeric material 119 to provide an optical power or other optical effect to provide correction for myopia, hyperopia, astigmatism, or other properties of the eye 110.

III. EXAMPLE INSTALLATION OF AN INTRA-OCULAR DEVICE IN AN EYE

Installation of an intra-ocular device or other objects as described herein into an eye of a user could be implemented in a variety of ways. Generally, installation of a device into the lens capsule or other space within an eye includes gaining surgical access to the lens capsule or other space by cutting through one or more membranes or other structures (e.g., using a sharpened edge, a surgical laser or some other means), removing a tissue to be replaced (e.g., removal of a natural lens via ultrasonic ablation/cutting and suction), and placement of the intra-ocular device or other object(s). Installation of an intra-ocular device as described herein to replace a natural lens and to detect accommodation forces applied via a lens capsule of an eye includes accessing the space within the lens capsule, removing the natural lens (i.e., the crystalline lens) from the lens capsule, and installing the intra-ocular device within the emptied lens capsule.

A patient can be prepared for surgical implantation of an intra-ocular device by application of anesthesia. Such anesthesia can include a local analgesic and a muscle relaxant and/or paralytic to prevent movement of the eye during the installation. An agent could be applied to dilate the iris or other elements of the eye in order to ease the installation of the intra-ocular device. Further, one or more properties of the eye (e.g., an optical power of the cornea and/or natural lens, a geometry of the eye, a degree of myopia, hyperopia, astigmatism, or other properties) could be measured to inform the installation and/or to inform configuration of the intra-ocular device. For example, one or more lenses could be added to the intra-ocular device based on a measured degree of myopia or other property of the eye. Additionally or alternatively, a particular intra-ocular device, having a specified optical power or other property, could be selected for installation based on a measured degree of myopia or other property of the eye. Further, calibration data or other programming of the intra-ocular device could be specified based on one or more measured properties of the eye Accessing the natural lens and lens capsule of an eye could include accessing the anterior chamber of the eye (i.e., the enclosed volume of the eye between the cornea and the iris and lens/lens capsule of the eye). This could include operating a diamond scalpel, surgical laser, or other cutting device to create one or more cuts through the cornea into the anterior chamber. In some examples, the anterior chamber could be inflated with air or some other fluid to facilitate access to and manipulation of the lens capsule.

To illustrate interaction with and manipulation of the natural lens and lens capsule of an eye to install an intra-ocular device, FIGS. 2A-2E are provided. FIGS. 2A-2E show cross-section views of the lens capsule 220, zonules 230 supporting the lens capsule, and other elements of an eye and/or intra-ocular device from the natural state of the eye (in FIG. 2A) through a number of steps through to an illustration of an intra-ocular device in the lens capsule 220 (in FIG. 2E). FIG. 2A illustrates the natural lens 210 intact within the intact lens capsule 220; the lens capsule 230 is held in place, and the shape of the natural lens 210 is partially determined by, forces exerted by the zonules 230 on and/or through the lens capsule 220. Note that the devices, methods, and embodiments described herein do not require that the natural lens 210, lens capsule 220, or other elements of the eye are intact and/or healthy. For example, the lens capsule 220, zonules 230, natural lens 210, or other elements of the eye could be damaged (e.g., have one or more holes of other missing elements or sections), have inclusions or other optical defects (e.g., the natural lens could include cataracts). In some examples, the natural lens 210 could already have been removed (e.g., during a previous procedure). For example, the natural lens 210 could have been removed and replaced with an intra-ocular lens during a previous procedure. Methods as described herein could be modified to include accessing and removing artificial and/or natural contents of such a lens capsule instead of accessing and removing the natural lens 210.

Access to the interior of the lens capsule 220 could be gained in a number of ways. For example, one or more cuts, holes, or other openings in the lens capsule 220 could be formed. FIG. 2B shows a hole 225 that has been formed in the anterior (i.e., frontward-facing, to the left in FIGS. 2A-2E) surface of the lens capsule 220. The hole 225 could be formed through a variety of methods, including operating a surgical laser to ablate tissues of the lens capsule 220 surrounding the hole 225. Alternatively, a mechanical implement (e.g., a bent needle) could be used to form an initial hole and subsequently to form a circular tear in the anterior surface of the lens capsule 220 that forms a closed hole 225 (e.g., according to the continuous curvilinear capsulorhexis technique). The removed anterior section of the lens capsule 220 could be extracted through a hole in the cornea.

The natural lens 210 could be removed in a variety of ways. For example, the natural lens could be cut, sectioned, dissected, emulsified, ablated, or otherwise damaged or destroyed, and fragments of the natural lens 210 remaining within the lens capsule 220 could be suctioned out or otherwise removed. FIG. 2C shows a vacancy 227 that has been formed within the lens capsule 220 following the removal of the natural lens 210. In some examples, some or all of the natural lens 210 could be destroyed and/or fragmented by applying ultrasonic vibrations to the natural lens 210 (e.g., using an ultrasonic probe inserted into the natural lens 210 through the hole 225 in the lens capsule 220 and a further hole or incision in the cornea). The natural lens 210 could additionally or alternatively be fragmented by applying one or more sharp or blunt tools to pull apart the fibers of the natural lens 210. Fragments of the natural lens 210 can be removed by suction (e.g., application of suction through a tube or other instrument inserted into the natural lens 210). Such suction could be performed while introducing a replacement fluid (e.g., a saline fluid) into the lens capsule 220 to maintain the volume and/or shape of the lens capsule 220. Such introduction of replacement fluid could be performed under the control of a microcontroller or by some other system such that the volume of fluid introduced is substantially equal to the volume of lens fragments and/or fluid removed by suction.

An intra-ocular device could be installed in the lens capsule 220 (e.g., within the vacancy 227). In some examples, this could include inserting a pre-formed intra-ocular device into the lens capsule 220 (e.g., inserting a folded or otherwise compacted flexible intra-ocular device into the vacancy 227 and allowing and/or manipulating the intra-ocular device to fill the vacancy 227 and to be in intimate contact with the inside surface of the lens capsule 220). In some examples, the intra-ocular device could be assembled and/or formed within the lens capsule 220. For example, a fluid could be injected into the lens capsule 220, and the fluid could be solidified to form a flexible polymeric material. Further, one or more additional elements (e.g., rigid or flexible fixed lenses or other optical elements, one or more rigid or flexible electronic lenses and associated electronics) could be disposed within such a polymeric material (e.g., by being positioned within a fluid before the fluid is solidified).

FIG. 2D shows a fluid 240 filling the lens capsule 220. The fluid could be introduced by injection, e.g., through a tube or other instrument configured to deliver the fluid into the lens capsule 220 through the hole 225 in the lens capsule 220 and a further hole or incision in the cornea. In some examples, the fluid 240 could be the replacement fluid introduced to replace fragments of the natural lens 210 removed by suction (i.e., the vacancy 227 within the lens capsule 220 would not be created by the removal of the natural lens 210 before introduction of the fluid 240). In some examples, the fluid 240 could be immiscible with the replacement fluid, and the replacement fluid could be suctioned from within the lens capsule 220 and/or displaced by the introduced fluid 240.

An intra-ocular device 250 could then be positioned within the fluid 240, and the fluid solidified to form a coupling 260 (e.g., a coupling 260 comprising a polymeric material) between the lens capsule 220 and the intra-ocular device 250 such that accommodation forces can be applied to the intra-ocular device 250, through the coupling 260, via the lens capsule 220. FIG. 2E shows an example in which intra-ocular device 250 may be positioned based on an optical axis of the eye (e.g., positioned such that an optical axis of the intra-ocular device 250 is substantially parallel and coincident with the optical axis of the eye). The intra-ocular device 250 could include one or more electronic lenses (e.g., nematic liquid-crystal lenses) configured to have an electronically-controllable optical power. The intra-ocular device 250 could further include one or more accommodation sensors configured to detect accommodation forces applied to the intra-ocular device 250 via the lens capsule 220 and coupling 260. The optical power of the electronic lens could be controlled based on accommodation forces detected using the accommodation sensor. Positioning of the intra-ocular device 250 could be performed manually or by an automated system (e.g., by an actuated tool configured to control the location of the intra-ocular device 250 within the fluid 240). Positioning of the intra-ocular device 250 could be performed based on an indication provided by an imaging system, e.g., an indication of the position of the intra-ocular device 250 relative to a desired positioning of the intra-ocular device 250 (e.g., such that an optical axis of the intra-ocular device 250 is aligned with the optical axis of the eye and/or such that the intra-ocular device 250 is located at a specified distance from the retina).

Positioning of the intra-ocular device 250 could be facilitated by haptic or other features of the optical device 250. For example, flexible springs (e.g., curved flexible wires or filaments of a polymer material) or other elements of the intra-ocular device 250 could be configured to apply forces against the inside of the lens capsule 220 and to position the intra-ocular device 250 within the lens capsule 220. Such flexible springs could be removed and/or destroyed after positioning the intra-ocular device 250 (e.g., could be destroyed and/or dissolved by a chemical agent in the fluid 240, could be photodecomposed by light applied to solidify the fluid and/or to destroy the springs, could be wholly or partially ablated by a beam of laser light). Additionally or alternatively, the flexible springs could be more compliant than the solidified fluid 240 such that the effect of the flexible springs on the coupling of accommodation forces between the lens capsule and the intra-ocular device 250 by the solidified fluid 240 is negligible. Removal and/or destruction of the flexible springs could occur before, during, and/or after solidification of the fluid 240.

The fluid 240 could be any one of a variety of fluids and/or combinations thereof that can be solidified to form a coupling between the lens capsule 220 and the intra-ocular device 250. The fluid could include a variety of monomers (e.g., silicone monomers) and other agents (e.g., photoinitiators) configured to solidify in response to some triggering factor (e.g., light, an introduced chemical agent, a chemical agent naturally present in the lens capsule 220 (e.g., water, certain ions, proteins)). For example, the fluid 240 could be configured to solidify into a silicone hydrogel. In some examples, the fluid 240 could be stable (i.e., could substantially not solidify) when disposed in the lens capsule and not exposed to a triggering factor (e.g., light). Alternatively, the fluid 240 could solidify spontaneously after being injected into the lens capsule 220 (e.g., could solidify in response to an agent present in the lens capsule, could include a solidifying agent (e.g., could be a mixture of a monomer and a solidifying agent mixed before being injected)).

The deposition/injection of the fluid 240, solidification of the fluid 240, and/or positioning of the intra-ocular device 250 and/or other elements on or within the fluid 240 could be performed in a number of stages. That is, an amount of fluid could be deposited and/or injected and solidified prior to the positioning of the intra-ocular device 250 and/or deposition and/or injection of further fluid. For example, an amount of the fluid could be injected to cover the base and walls of the lens capsule 220. The intra-ocular device 250 could then be positioned on the deposited fluid and aligned with the optical axis of the eye. Further fluid could then be deposited on top of the intra-ocular device 250 such that the fluid fills the lens capsule 220. The fluid 240 could then be solidified (e.g., by exposure to light) to form a coupling between the intra-ocular device 250 and the lens capsule 220. Other schemes for depositing and/or injecting fluid, solidifying deposited and/or injected fluids, positioning intra-ocular devices, or other components thereof, or other steps are anticipated.

Figure 3:
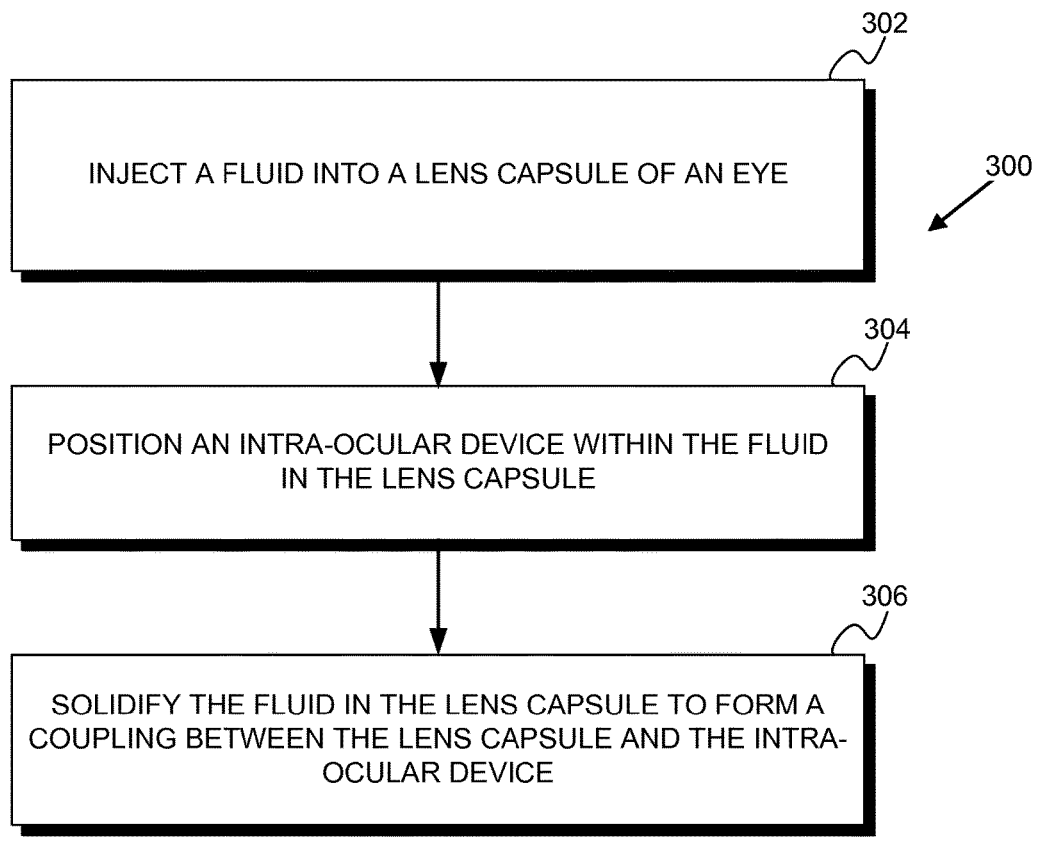
FIG. 3 is a flowchart of an example process for installing an intra-ocular device in a lens capsule of an eye.

FIG. 3 is a flowchart of a method 300 for installing an intra-ocular device in a lens capsule of an eye from which a natural and/or artificial lens has already been removed. The intra-ocular device includes (i) an electronic lens having an optical power that can be controlled within a range of optical powers and whose optical power is controlled in part by an electrical signal applied to the electronic lens, (ii) an accommodation sensor configured to detect accommodation forces applied to the intra-ocular device via the lens capsule of the eye, and (iii) a controller operatively coupled to the electronic lens and the accommodation sensor and configured to apply an electronic signal to the electronic lens to control the optical power of the electronic lens based on the accommodation forces detected using the accommodation sensor. The intra-ocular device and elements thereof could be configured and/or operated as described herein. Further, the intra-ocular device could include additional components configured to provide some functionality. For example, the intra-ocular device could include a polymeric material that contains the electronic lens, accommodation sensor, and controller and that is configured to form a coupling between the lens capsule and the accommodation sensor and/or electronic lens, or some other components or combinations thereof.

The method 300 includes injecting a fluid into the lens capsule of the eye (302). This could include injecting the fluid into the lens capsule after removal of a natural lens of the eye from the lens capsule. In some examples, injecting a fluid into the lens capsule of the eye (302) could include injecting the fluid at the same time that fragments of the natural lens of the eye are suctioned or otherwise removed from the lens capsule. This could include introducing the fluid at a rate substantially equal to a rate of removal of the fragments of the natural lens and/or some other fluids (e.g., the injected fluid and/or some other replacement fluid(s)). In some examples, injecting a fluid into the lens capsule of the eye (302) could include mixing two or more different fluids (e.g., two fluids comprising a two-part epoxy or other two-part substance configured to begin polymerizing or otherwise solidifying upon mixture) and injecting the mixed fluids into the lens capsule. Injecting a fluid into the lens capsule of the eye (302) could include filling the lens capsule, applying the fluid in one or more stages (e.g., applying an amount of the fluid, positioning the intra-ocular device on/within the fluid, and then applying more fluid), applying the fluid to a particular region(s) within the lens capsule (e.g., to the base and walls of the lens capsule), or according to some other application.

The method 300 includes positioning the intra-ocular device within the fluid in the lens capsule (304). Positioning the intra-ocular device (304) could be performed manually or by an automated system (e.g., by an actuated tool configured to control the location of the intra-ocular device within the fluid). Positioning of the intra-ocular device (304) could be performed based on an indication provided by an imaging system, e.g., an indication of the position of the intra-ocular device relative to a desired positioning of the intra-ocular device (e.g., such that an optical axis of the intra-ocular device is aligned with the optical axis of the eye and/or such that the intra-ocular device is located at a specified distance from a retina of the eye). Positioning of the intra-ocular device (304) could be facilitated by haptic or other features of the intra-ocular device. For example, flexible springs (e.g., curved flexible wires or filaments of a polymer material) or other elements of the intra-ocular device could be configured to apply forces against the inside of the lens capsule to position the intra-ocular device within the lens capsule.

The method 300 further includes solidifying the fluid in the lens capsule to form a coupling between the lens capsule and the intra-ocular device (306). This could include introducing and/or exposing the fluid to a factor such that the fluid solidifies. For example, the fluid could include a photo-polymerizing monomer (e.g., a silicone monomer) and/or a mixture of a monomer (e.g., a silicone monomer) and a photo-initiating agent and solidifying the fluid (306) could include exposing the fluid to a light (e.g., a light at a specified wavelength and having an intensity greater than a specified level) such that the fluid solidifies (e.g., into a silicone hydrogel). Other methods of solidifying the fluid (306) are anticipated. Further, the fluid could be injected and/or solidified in multiple phases (e.g., a first amount of fluid could be injected and/or solidified, and a second amount of fluid could be subsequently injected and/or solidified).

The method 300 could include additional steps or elements in addition to those depicted in FIG. 3 (i.e., 302, 304, 306). Further, alternative embodiments of the listed steps are anticipated.

IV. EXAMPLE INTRA-OCULAR DEVICE

Figure 4:
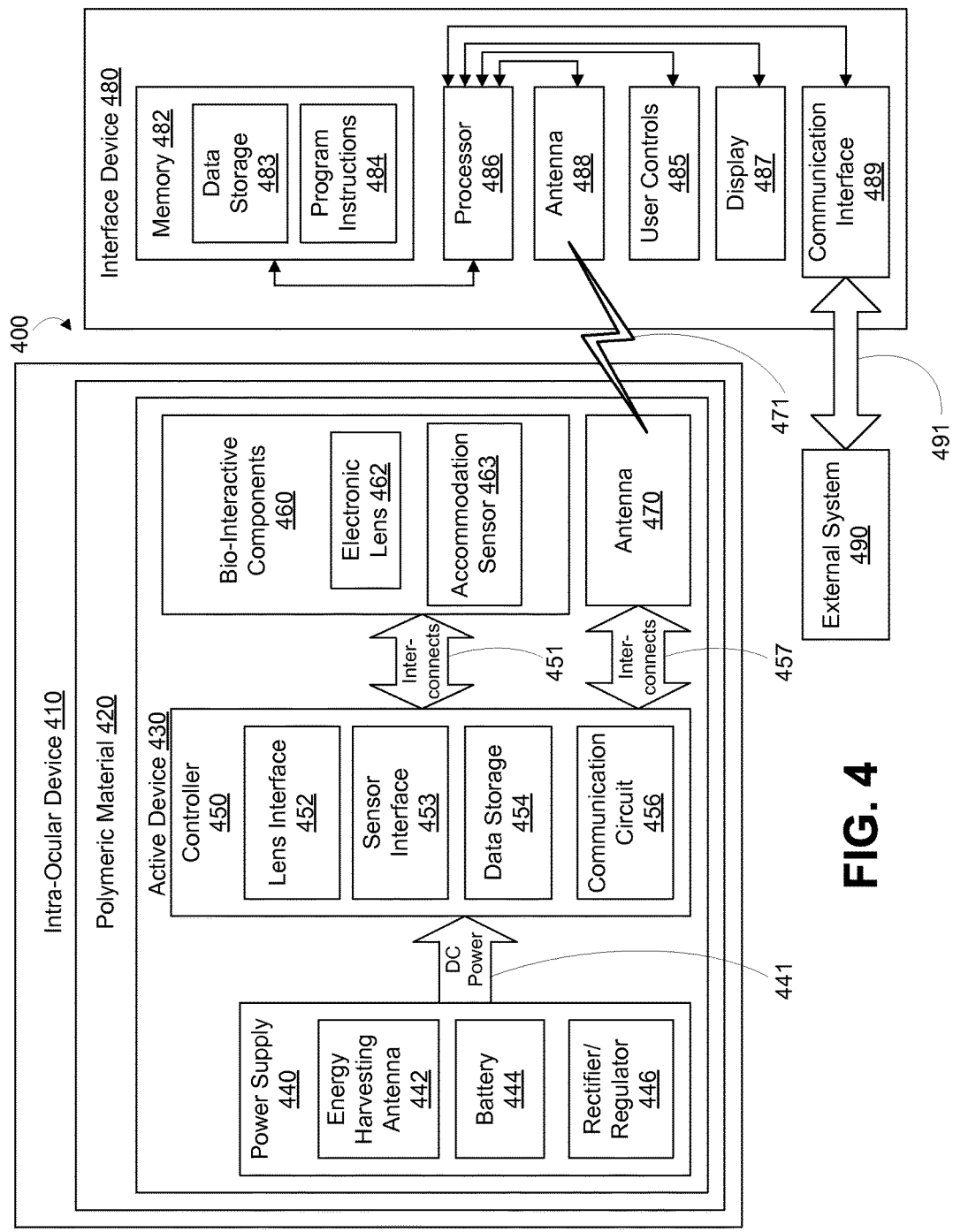
FIG. 4 is a block diagram of an example system that includes an intra-ocular device in wireless communication with an external reader.

FIG. 4 is a block diagram of a system 400 that includes an intra-ocular device 410 in wireless communication with an external interface device 480. The exposed regions of the intra-ocular device 410 are made of a polymeric material 420 formed to be in intimate contact with the inside surface of the lens capsule of an eye. An active device 430 is embedded in the polymeric material 420 and contains a power supply 440, a controller 450, bio-interactive components 460, and a communication antenna 470. The bio-interactive components 460 are operated by the controller 450. The power supply 440 supplies operating voltages to the controller 450 and/or the bio-interactive components 460. The antenna 470 is operated by the controller 450 to communicate information to and/or from the intra-ocular device 410. Because the intra-ocular device 410 includes electronics and is configured to be surgically installed within an eye, it is also referred to herein as an ophthalmic electronics platform.

To couple accommodation forces from a lens capsule to the active device 430, the polymeric material 420 can have a shape corresponding to the shape of the lens capsule. Additionally or alternatively, the polymeric material 420 could be adhered to the inside surface of the lens capsule. In some examples, this could include forming the polymeric material 420 outside of the lens capsule, in a shape corresponding to the lens capsule and inserting the pre-formed polymeric material 420 (and active device 430 contained therein) into the lens capsule (e.g., inserting a folded or otherwise compacted flexible intra-ocular 410 device into the lens capsule and allowing and/or manipulating the intra-ocular device 410 to be in intimate contact with the inside surface of the lens capsule). In some examples, the intra-ocular device 410 could be assembled and/or formed within the lens capsule. For example, a fluid could be injected into the lens capsule, and the fluid could be solidified to form the polymeric material 420. Further, the active device 430 could be disposed within such an injected fluid prior to solidification.

The polymeric material 420 and/or active device 430 can include one or more biocompatible materials, such as those employed for use in contact lenses, intra-ocular lenses, or other implanted ophthalmic applications. The polymeric material 420 can optionally be formed in part from such biocompatible materials or can include an outer coating with such biocompatible materials. The polymeric material 420 can include materials configured to permit diffusion of fluids, such as silicone hydrogels and the like. In some instances, the polymeric material 420 can have a specified index of refraction to provide a vision-correcting optical power.

The active device 430 can include one or more substrates suitable for mounting the bio-interactive components 460, the controller 450, the power supply 440, and the antenna 470. Such substrates can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide, a matted network of silver nanowires) can be patterned on the substrates to form circuitry, electrodes, etc. For example, the antenna 470 or one or more electrodes of the electronic lens 462 can be formed by depositing a pattern of gold, silver nanowires, or another conductive material on a surface of a substrate. Similarly, interconnects 451, 457 between the controller 450 and the bio-interactive components 460, and between the controller 450 and the antenna 470, respectively, can be formed by depositing suitable patterns of conductive materials on a substrate. A combination of microfabrication techniques including, without limitation, the use of photoresists, masks, deposition techniques, and/or plating techniques can be employed to pattern materials on a substrate.

Such a substrate can be a relatively rigid material, such as polyethylene terephthalate (PET), parylene, polymethyl methacrylate (PMMA), or another material sufficient to structurally support the circuitry and/or electronics. Additionally or alternatively, a substrate could be wholly or partially flexible (e.g., to allow coupled accommodation forces to change an optical power of fixed and/or electronic lenses of the active device 430, to allow detection of the accommodation forces by detecting a deformation of elements of the active device 430), with the flexible elements composed of silicones, hydrogels, or other flexible materials.

One or more additional lenses (i.e., lenses additional to the electronic lens 462) could be included in the active device 430 and/or embedded in the polymeric material 420. Such additional lenses could be configured to provide an additional optical power in combination with a controllable optical power of the electronic lens 462. Such an additional optical power could be provided to correct some optical defect of the eye (e.g., to correct a myopia, a hyperopia, an astigmatism) and/or to correct for the loss of the optical power of the natural lens due to the removal of the natural lens. The optical power or other properties of such additional lenses could be specified based on one or more measurements of the eye (e.g., an effective optical power of the cornea, an effective optical power of the removed natural lens, a curvature of the retina, a distance between the retina and the cornea/intra-ocular lens 410, a lens prescription corresponding to the eye). In some examples, one or more of the additional lenses could have a fixed optical power and/or be rigid. Additionally or alternatively, one or more of the additional lenses could be flexible and could be configured to have an optical power that changes due to changes in the geometry of the additional lens. Such changes in the geometry of the lens could be caused by accommodation forces applied to the additional lens, e.g., by being coupled from the lens capsule through the polymeric material 420.

The power supply 440 is configured to power the controller 450 and bio-interactive components 460. The power supply 440 is configured to provide power from a battery 444 (e.g., a flexible, thin-film, and/or solid-state battery) to the controller 450 and bio-interactive components 460. The power supply 440 is additionally configured to harvest energy to recharge the battery 444. For example, a radio-frequency energy-harvesting antenna 442 can capture energy from incident radio radiation. Furthermore, an inertial power scavenging system can be included to capture energy from ambient vibrations and/or eye motion. The energy harvesting antenna 442 can optionally be a dual-purpose antenna that is also used to communicate information to the interface device 480. That is, the functions of the communication antenna 470 and the energy harvesting antenna 442 can be accomplished with the same physical antenna. Recharging the battery 444 can include applying a controlled current, a controlled voltage, or electrical energy having some other specified property to the battery 444.

A rectifier/regulator 446 can be used to condition the captured energy to a stable DC supply voltage 441 that is supplied to the controller 450 and/or used to recharge the battery 444. For example, the energy harvesting antenna 442 can receive incident radio frequency radiation. Varying electrical signals on the leads of the antenna 442 are output to the rectifier/regulator 446. The rectifier/regulator 446 rectifies the varying electrical signals to a DC voltage and regulates the rectified DC voltage to a level suitable for operating the controller 450 and/or recharging the battery 444. The rectifier/regulator 446 can include one or more energy storage devices to mitigate high frequency variations in the ambient energy gathering antenna 442. For example, one or more energy storage devices (e.g., a capacitor, an inductor, etc.) can be connected in parallel across the outputs of the rectifier 446 to regulate the DC supply voltage 441 and configured to function as a low-pass filter.

The controller 450 can include logic circuitry configured to operate the bio-interactive components 460 so as to interact with a biological environment of the intra-ocular device 410. The interaction could involve the use of one or more components, such as an electronic lens 462, in bio-interactive components 460 to focus light in a controlled manner such that an eye containing the intra-ocular device 410 can image objects in the environment of the eye in-focus.

In one example, the controller 450 includes a lens interface module 452 that is configured to operate the electronic lens 462. The electronic lens 462 can be operated to have a controlled optical power (e.g., to have a controllable focal length). For example, the lens interface 452 could include a lens voltage source configured to apply a specified electronic signal (e.g., an alternating voltage waveform having a specified amplitude, mean voltage, frequency, duty cycle, or some other specified properties) across two or more electrodes of the electronic lens 462 such that the refractive index of a liquid crystal material (e.g., a nematic liquid crystal) of the electronic lens 462 has a controlled value related to the applied electronic signal. For example, the amplitude of an alternating voltage applied across electrodes of the electronic lens 462 could be related to the refractive index of the liquid crystal, which in turn could be related to the optical power of the electronic lens 462. Alternatively, the lens interface module 452 could include other electronic components configured to operate other elements of an electronic lens (e.g., piezo elements configured to change a geometry of the lens, microfluidic elements configured to displace fluids into and/or out of chambers or reservoirs of the lens, electro-wetting materials configured to change a shape by controlling a degree of wetting of elements of the lens). Additionally or alternatively, one or more electronic elements or systems configured to operate the electronic lens 462 could be disposed as part of the bio-interactive components 460 or as part of some other aspect of the intra-ocular device 410.

The controller 450 also includes a sensor interface 453 that is configured to operate the accommodation sensor 463. This could include applying detecting one or more properties of the accommodation sensor 463 (e.g., a resistance, an impedance, a voltage, a capacitance) that are related to accommodation forces (e.g., to a strain detected by an accommodation sensor that includes a strain-sensitive element) exerted via the lens capsule and coupled to the active device 430 by the polymeric material 420. For example, the sensor interface 453 could include a current (or voltage) source configured to apply a specified current (or voltage) to the accommodation sensor 463, and further configured to detect a voltage across (or current through) the accommodation sensor related to the applied current (or voltage) and to the accommodation force detected by the accommodation sensor 463. The sensor interface 453 could include a resistive, capacitive, or other type of bridge circuit to allow high-sensitivity measurement of one or more properties of the accommodation sensor 463. For example, the accommodation sensor 463 could include a resistive or other variety of strain sensor, and the sensor interface 453 could include a resistive or other type of bridge circuit that is connected to the strain sensor such that the strain sensor forms one of the legs of the bridge circuit. The sensor interface 453 could include oscillators or other waveform generators configured to apply a voltage and/or current waveform to the accommodation sensor 463 to allow for the detection of a capacitance, impedance, or some other property of the accommodation sensor 463. Additional elements and operations of the sensor interface 453 to measure one or more properties of the accommodation sensor 463 are anticipated.

The controller 450 can also include a communication circuit 456 for sending and/or receiving information via the antenna 470. The communication circuit 456 can optionally include one or more oscillators, mixers, frequency injectors, etc. to modulate and/or demodulate information on a carrier frequency to be transmitted and/or received by the antenna 470. In some examples, the eye-mountable device 410 is configured to indicate an output from the accommodation sensor 463 by modulating an impedance of the antenna 470 in a manner that is perceivably by the interface device 480. For example, the communication circuit 456 can cause variations in the amplitude, phase, and/or frequency of backscatter radiation from the antenna 470, and such variations can be detected by the interface device 480.

The controller 450 is connected to the bio-interactive components 460 via interconnects 451. For example, where the controller 450 includes logic elements implemented in an integrated circuit to form the lens interface module 452 and/or data storage 454, a patterned conductive material (e.g., gold, platinum, palladium, titanium, copper, aluminum, silver, metals, silver nanowires, combinations of these, etc.) can connect a terminal on the chip to the bio-interactive components 460. Similarly, the controller 450 is connected to the antenna 470 via interconnects 457.

It is noted that the block diagram shown in FIG. 4 is described in connection with functional modules for convenience in description. However, embodiments of the intra-ocular device 410 can be arranged with one or more of the functional modules ("sub-systems") implemented in a single chip, integrated circuit, and/or physical feature. For example, while the rectifier/regulator 446 is illustrated in the power supply block 440, the rectifier/regulator 446 can be implemented in a chip that also includes the logic elements of the controller 450 and/or other features of the embedded electronics in the intra-ocular device 410. Thus, the DC supply voltage 441 that is provided to the controller 450 from the power supply 440 can be a supply voltage that is provided on a chip by rectifier and/or regulator components the same chip. That is, the functional blocks in FIG. 4 shown as the power supply block 440 and controller block 450 need not be implemented as separated modules. Moreover, one or more of the functional modules described in FIG. 4 can be implemented by separately packaged chips electrically connected to one another.

Additionally or alternatively, the energy harvesting antenna 442 and the communication antenna 470 can be implemented with the same physical antenna. For example, a loop antenna can both harvest incident radiation for power generation and communicate information via backscatter radiation.

The interface device 480 includes an antenna 488 (or group of more than one antenna) to send and receive wireless signals 471 to and from the intra-ocular device 410. The interface device 480 also includes a computing system with a processor 486 in communication with a memory 482. The interface device 480 can also include one or more of user controls 485, a display 487, and a communication interface 489. The memory 482 is a non-transitory computer-readable medium that can include, without limitation, magnetic disks, optical disks, organic memory, and/or any other volatile (e.g. RAM) or non-volatile (e.g. ROM) storage system readable by the processor 486. The memory 482 can include a data storage 483 to store indications of data, such as sensor readings (e.g., related to the accommodation sensor 463), program settings (e.g., to adjust behavior of the intra-ocular device 410 and/or external reader 480), etc. The memory 482 can also include program instructions 484 for execution by the processor 486 to cause the interface device 480 to perform processes specified by the instructions 484. For example, the program instructions 484 can cause interface device 480 to perform any of the function described herein. For example, program instructions 484 may cause the interface device 480 to provide a user interface that allows for retrieving information communicated from the intra-ocular device 410 (e.g., sensor outputs or other information related to the accommodation sensor 463) by displaying that information on the display 487 in response to commands input through the user controls 485. In another example, program instructions 484 may cause the interface device 480 to provide a user interface that allows for setting and/or changing (e.g., increasing or decreasing by a specified amount) a controlled optical power of the electronic lens 462 by transmitting commands or other information to the intra-ocular device 410 using the antenna 488 in response to commands input through the user controls 485. The interface device 480 can also include one or more hardware components for operating the antenna 488 to send and receive the wireless signals 471 and/or wireless power to and from the intra-ocular device 410. For example, oscillators, frequency injectors, encoders, decoders, amplifiers, filters, etc. can drive the antenna 488 according to instructions from the processor 486.

The interface device 480 can also be configured include a communication interface 489 to communicate signals via a communication medium 491 to and from a remote system 490. For example, the remote system 490 may be a smart phone, tablet computer, laptop computer, or personal computer, and communication interface 489 and communication medium 491 may be a Bluetooth module and wireless Bluetooth communication signals, respectively. In this example, the interface device 480 may be configured to send accommodation forces collected by the accommodation sensor 460 to the smart phone, tablet computer, laptop computer, or personal computer for storage and offline analysis. In another example, the remote system 490 is a server at a clinic or optometrist's office, the communication interface 489 is a WiFi radio module, and the communication medium 491 is elements of the internet sufficient to enable the transfer of data between the remote server and the WiFi radio module. An optometrist may use this data to make determinations or diagnoses related to the subject's condition. Further, the interface device 480 may be configured to receive signals from a remote server, such as instructions sent by a physician at a remote location to, for example, change programming of the intra-ocular device 410 relating detected levels of accommodation forces to controlled optical powers of the electronic lens 462. Communication interface 489 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The interface device 480 can be a smart phone, digital assistant, or other portable computing device with wireless connectivity sufficient to provide the wireless communication link 471. The interface device 480 can also be implemented as an antenna module that can be plugged into a portable computing device, such as in an example where the communication link 471 operates at carrier frequencies not commonly employed in portable computing devices. In some instances, the interface device 480 is a special-purpose device configured to be worn relatively near a user's eye and/or disposed on, within, or near a bed used by the user to allow the wireless communication link 471 to operate and/or power the intra-ocular device 410 with a low power budget. For example, the interface device 480 can be integrated in a piece of jewelry such as a necklace, earring, etc. or integrated in an article of clothing worn near the head, such as a hat, headband, etc. The interface device 480 could also be implemented in eye glasses or a head-mounted display. In some examples, the interface device 480 or some set of elements thereof could be configured to be placed within a pillow, attached to a headboard, secreted beneath bed sheets, or otherwise disposed proximate to a user's head when the user is sleeping such that the interface device 480 can power the intra-ocular device 410 (e.g., to recharge the battery 444 of the intra-ocular device 410) while the user is sleeping.

The controller 452 can be operated to measure an accommodation force applied to the intra-ocular device 410 via the lens capsule using the accommodation sensor 463. For example, a resistance of the accommodation sensor 463 could be related to a strain detected by the accommodation sensor, which could, in turn, be related to an accommodation force applied to the intra-ocular device 410 via the lens capsule. In other examples, a deformation, stress, pressure, or other physical property of an element of the intra-ocular device 410 (e.g., of the accommodation sensor 436) and/or of the environment of the intra-ocular device 410 could be detected by the accommodation sensor 463 and used to measure and/or determine an accommodation force. The controller 450 can, responsive to detecting an accommodation force, control the optical power of the electronic lens 463 (e.g., by operating the lens interface 452 to apply an electrical signal having one or more properties specified based on the detected accommodation force).

Generating an electrical signal or other signal (e.g., a fluid flow and/or a fluid pressure in a microfluidic lens) to control the optical power of the electronic lens 462 based on a measurement made using the accommodation sensor 463 could be done by using calibration data. That is, the controller 450 could use stored calibration data (e.g., stored in the data storage 454 of the controller 450) to determine one or more properties (e.g., an amplitude, a frequency, a duty cycle) of the electrical signal based on a detected value of accommodation force. Such calibration data could include one or more values specifying a linear or nonlinear relationship between detected accommodation forces and properties of the electrical signal (e.g., a slope and an offset of a linear relationship, two or more parameters describing a polynomial of a nonlinear relationship). Such calibration data could include a lookup table specifying a plurality of properties of the electrical signal corresponding to a respectively plurality of detected accommodation force levels and/or ranges of levels. Such calibration data could be updated based on updated calibration data received from the interface device 480 or form some other device using the antenna 470, using a light sensor of the intra-ocular device 410 configured to act as part of an optical communications channel, or according to some other method.

Detected values of accommodation forces applied by the lens capsule and detected using the accommodation sensor 463 could be transmitted (e.g., using the antenna 470) to the interface device 480 and used for some application. In some applications, such transmitted accommodation force information could be used as part of a human interface to a computer, e.g., to determine the distance from the user of an object the user is attempting to focus on. For example, such detected accommodation force information could be used to change a simulated focus and/or depth-of-field of a virtual scene presented to the user. In some examples, such detected accommodation force data could be used to update calibration data used to operate the intra-ocular device 410. For example, a user could indicate (e.g., using the user controls 485 of the interface device 480) that an optical power of the electronic lens 462 should be increased. In some examples, this indication could be used to update the calibration data, e.g., to update the calibration data such that detection of a corresponding value of the applied accommodation force in the future should cause the electronic lens 462 to be operated to have the increased optical power. Additionally or alternatively, detected accommodation forces and corresponding controlled properties of the lens-controlling electrical signal could be recorded and used to update the calibration data automatically. For example, the calibration data could be updated such that less accommodative 'effort' (i.e., a smaller applied accommodation force) is required to cause the electronic lens to increase/decrease its optical power by a particular amount.

In some embodiments, the system 400 can operate to non-continuously ("intermittently") supply energy to the intra-ocular device 410 to power the controller 450 and components 460. For example, radio frequency radiation 471 can be supplied to power the intra-ocular device 410 when the user is sleeping and thus proximate to an interface device 480 configured to be positioned on or within a bed used by the user. In such an example, the supplied radio frequency radiation 471 can be used to recharge the battery 444 of the intra-ocular device 410. By periodically providing power to the intra-ocular device 410 (e.g., by supplying radio frequency radiation 471 while the user sleeps proximate to the interface device 480), the battery 444 of the intra-ocular device 410 can be recharged and used to power the intra-ocular device 410 during periods of time when the user is not proximate to the interface device 480, such that the intra-ocular device 410 can operate when the user is not proximate to the interface device 480 (e.g., while performing activities of daily living away from the interface device 480 and/or a bed on or within which the interface device 480 is disposed). In other embodiments, the system 400 can operate continuously and supply energy to the intra-ocular device 410 to power the controller 450 and components 460. In such instances, the interface device 480 may be configured as a wearable device, as part of eyeglasses, a necklace, a hat, or some other object that can be worn by a user and/or disposed on or within clothes worn by the user.

Figure 5A:
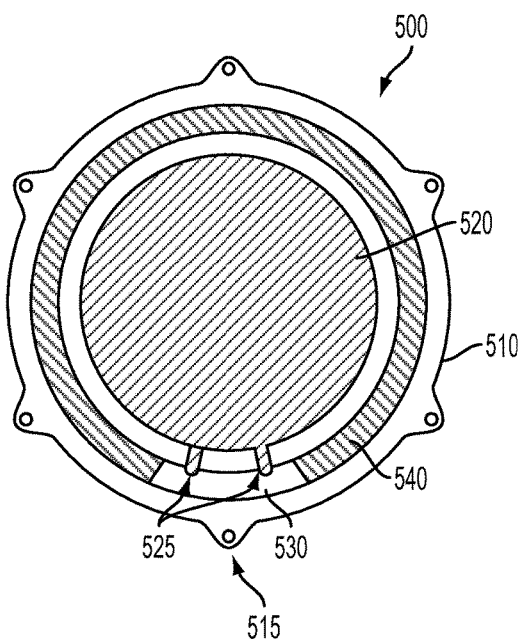
FIG. 5A is a top view of an example intra-ocular device.
Figure 5B:
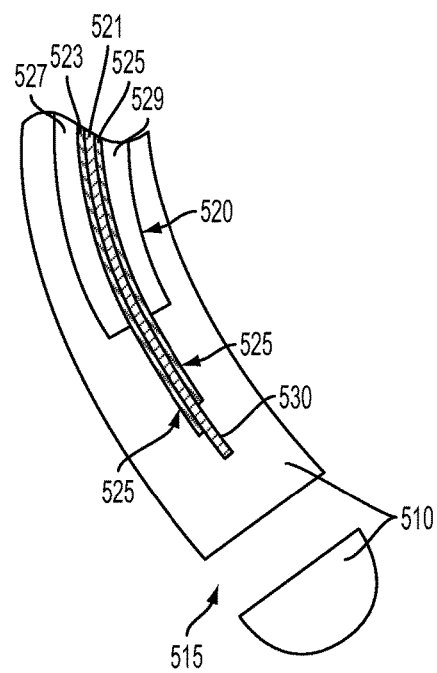
FIG. 5B is side cross-section view of part of the example intra-ocular device shown in FIG. 5A.
Figure 5C:
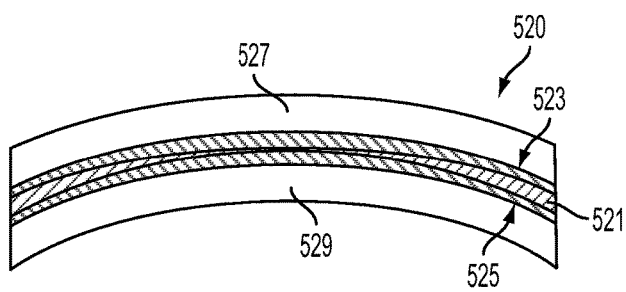
FIG. 5C is side cross-section view of elements of the example intra-ocular device shown in FIG. 5A.

FIG. 5A is a bottom view of an example intra-ocular device 500. FIG. 5B and FIG. 5C are cross-section views of elements of the example intra-ocular device 500 shown in FIG. 5A. It is noted that relative dimensions in FIGS. 5A, 5B, and 5C are not necessarily to scale, but have been rendered for purposes of explanation only in describing the arrangement of the example intra-ocular device 500. The intra-ocular device 500 is formed of a substrate material 510 shaped as a curved disk. The substrate material 510 can be a substantially transparent material to allow incident light to be transmitted to the retina while the intra-ocular device 500 is disposed within the lens capsule of the eye. The substrate material 510 can be partially composed of a relatively rigid material, such as polyethylene terephthalate (PET), parylene, polymethyl methacrylate (PMMA), or another material sufficient to structurally support circuitry and/or electronics of the intra-ocular device 500. Additionally or alternatively, the substrate material 510 could be wholly or partially composed of flexible materials (e.g., to allow coupled accommodation forces to change an optical power of fixed and/or electronic lenses of the intra-ocular device 500, to allow detection of accommodation forces by detecting a deformation of elements of the intra-ocular device 500), with the flexible elements of the intra-ocular device 500 being composed of silicones, hydrogels, or other flexible materials. The substrate material 510 can be formed with a curved or other specified shape in a variety of ways. For example, techniques similar to those employed to form vision-correcting intra-ocular lenses, such as heat molding, injection molding, spin casting, etc. can be employed to form the substrate material 510.

Components of the intra-ocular device 500 are embedded in the substrate material 510. Opaque or partially transparent components can be embedded to be situated along the outer periphery of the substrate material 510, away from the center region. Such opaque or partially transparent components can be positioned to not interfere with vision because they are too close to the retina to be in focus and by being positioned away from the center region where incident light is transmitted to the light-sensing portions (i.e., light-sensitive cells of the retina) of the eye. Additionally or alternatively, components embedded in the substrate material 510 (e.g., electrodes 525 of an electronic lens 520) could be wholly or partially transparent. In some examples, such components could be electrically conductive and transparent by being composed of a thin layer of a transparent conductor (e.g., indium tin oxide, ITO). Such components could further be made flexible (e.g., to allow for a deformation of the electronic lens 520 by accommodation forces applied via the lens capsule) by being composed of a flexible transparent conductor. Such flexible transparent conductors could be composed of a plurality of flexible silver nanowires.

The substrate material 510 could be formed from multiple pieces, one or more of which could include a flat surface configured to allow the mounting of components of the intra-ocular device 500 (e.g., controller electronics 530, the electronic lens 520, an antenna 540). Such a flat surface of the substrate material 510 could be a platform for mounting electronics such as chips (e.g., via flip-chip mounting) and for patterning conductive materials (e.g., via deposition techniques) to form electrodes, antenna(e), sensors (e.g., an accommodation sensor) and/or connections. One or more of such connections, antenna(e), sensors, or other elements could include a flexible transparent conductor composed of a plurality of flexible silver nanowires. Such a flexible transparent conductor could be formed by depositing a solution containing the plurality of flexible silver nanowires in a specified region (e.g., a region specified to contain a connection) and evaporating or otherwise removing a carrier fluid or solvent of the deposited solution, leaving the plurality of flexible silver nanowires. Additional or alternative methods of forming a flexible conductor composed of a plurality of flexible silver nanowires, or of forming some other conductors on the substrate material 510, are anticipated.

A loop antenna 540, controller 530, and electronic lens 520 are disposed in the substrate material 510. The controller 530 can be a chip including logic elements configured to operate the electronic lens 520, accommodation sensor (not shown) and the loop antenna 540. The controller 530 is electrically connected to the electronic lens 520 by interconnects 525 formed as extensions of first 523 and second 525 electrodes of the electronic lens 520. The first 523 and second 525 electrodes, the loop antenna 540, and any conductive electrodes (e.g., for an accommodation sensor, etc.) can be formed from conductive materials patterned on or within substrate material 510 by a process for precisely patterning such materials, such as deposition, lithography, etc. The conductive materials patterned on the substrate material 510 can be, for example, gold, platinum, palladium, titanium, carbon, aluminum, copper, silver, silver-chloride, indium tin oxide, a plurality of flexible silver or other-metal nanowires, conductors formed from noble materials, metals, combinations of these, etc.

The loop antenna 540 can be a layer of conductive material patterned to form a conductive ring. In some instances, the loop antenna 540 can be formed without making a complete loop. For instance, the loop antenna 540 can have a cutout to allow room for the controller 530 and/or accommodation sensor, as illustrated in FIG. 5A. However, the loop antenna 530 can also be arranged as a continuous strip of conductive material that wraps entirely around the substrate material 510 one or more times. For example, a strip of conductive material with multiple windings can be patterned on a side of the substrate material 510 opposite the controller 530. Interconnects between the ends of such a wound antenna (e.g., the antenna leads) can be passed through the substrate material 510 to the controller 530. An antenna of an intra-ocular device 500 could take other forms, as well. For example, an antenna could be a patch antenna, a fractal antenna, or some other form of antenna. Elements of such an antenna could be formed from transparent conductors, such that such antenna elements could be disposed across the area of the intra-ocular device 500 (e.g., across an area through which light is transmitted toward the retina of the eye). Further, elements of an antenna could be used for other functions of the intra-ocular device 500. For example, one of the electrodes 523, 525 of the electronic lens 520 could be used as a ground plane or other element of an antenna. Additionally or alternatively, elements of the loop antenna 540 could be used as part of an accommodation sensor. For example, accommodation forces applied to the intra-ocular device 500 could cause deformation of the intra-ocular device 500 such that the length of the loop antenna 540 is changed. Such a change in length could cause a change in the resistance of the loop antenna 540, and the resistance of the loop antenna 540 could be measured by the controller 530 such that the loop antenna 540 forms part of the accommodation sensor.

As illustrated in FIGS. 5A-5C, the electronic lens 520 includes a layer of liquid crystal 521 (e.g., a nematic liquid crystal) disposed between two electrodes 523, 525. Application of an alternating electrical signal across the electrodes 523, 525 can control the refractive index of the liquid crystal, thus controlling the optical power of the electronic lens 520. The refractive index of the liquid crystal could be related to the amplitude of the alternating electrical signal, the mean voltage of the electrical signal, the frequency of the electrical signal, the duty cycle of the electrical signal, or some other properties of the electrical signal according to the configuration of the liquid crystal and/or electrodes 523, 525. The electrodes 523, 525 could be composed of a transparent conductor (e.g., indium tin oxide) or a conductor that is both flexible and transparent (e.g., a plurality of flexible silver nanowires, and/or nanowires composed of some other metal, metal alloy, or other conductive material). Further, the liquid crystal layer 521 could include a nematic liquid crystal, a twisted nematic liquid crystal, a cholesteric liquid crystal, a blue phase liquid crystal, or some other type or phase of liquid crystal according to an application.

Note that the use of a controlled-refractive-index liquid-crystal electronic lens is intended as a non-limiting illustrative example. Other electronic lenses could be use instead of or in addition to a liquid-crystal electronic lens as described herein. For example, an electronic lens containing a plurality of independently-controllable light-modulating elements (e.g., liquid crystal elements, micromirrors) could be formed into a spatial light modulator and operated to control an optical power or other optical property of the intra-ocular device 500. An electronic lens could be configured to change a geometry or shape of the electronic lens to control an optical power of the electronic lens. This could include one or more micro-fluidic pumps, reservoirs, chambers, or other elements configured to increase a thickness, control a surface shape, or control some other property of the geometry of the electronic lens. The electronic lens could include one or more piezoelectric elements or other actuators configured to control a shape, thickness, or other properties of the electronic lens related to the optical power of the electronic lens. An electro-wetting material or element could be included in an electronic lens and operated to control a thickness or other property of the electronic lens (e.g., by drawing a fluid to the electro-wetting material or element) related to the optical power of the electronic lens. Additional or alternative configurations and/or combinations of elements are anticipated to provide an electronic lens that could be included in an intra-ocular device as described herein.

The intra-ocular device 500 additionally includes two additional lenses 527, 529 disposed opposite the electronic lens 520 within the substrate material 510 (as shown in FIGS. 5B and 5C). The additional lenses 527, 529 are configured to provide an additional optical power in combination with a controllable optical power of the electronic lens 520. Such an additional optical power could be provided to correct some optical defect of the eye (e.g., to correct a myopia, a hyperopia, an astigmatism) and/or to correct for the loss of the optical power of the natural lens due to the removal of the natural lens. The optical power or other properties of the additional lenses 527, 529 could be specified based on one or more measurements of the eye (e.g., an effective optical power of the cornea, an effective optical power of the removed natural lens, a curvature of the retina, a distance between the retina and the cornea/electronic lens 520, a lens prescription corresponding to the eye). In some examples, one or more of the additional lenses 527, 529 could have a fixed optical power and/or be rigid. Additionally or alternatively, one or more of the additional lenses 527, 529 could be flexible and could be configured to have an optical power that changes due to changes in the geometry of the additional lens 527, 529. Such changes in the geometry of the lens could be caused by accommodation forces applied to the additional lens 527, 529 via the lens capsule.

Figure 5F:
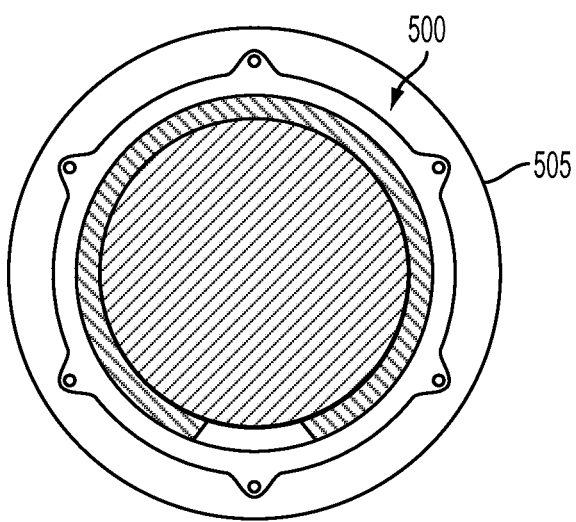
FIG. 5F is side cross-section view of the example intra-ocular device of FIG. 5A disposed within a lens capsule of an eye.
Figure 5F:
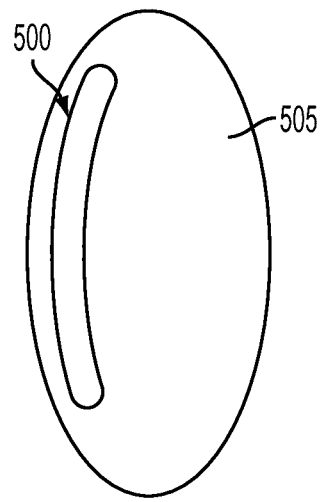
Figure 5F:
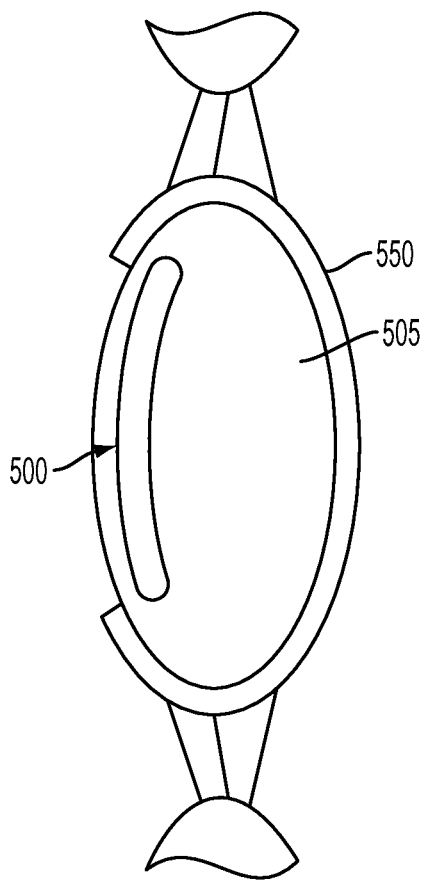

FIGS. 5D and 5E show front and side cross-section views, respectively, of the intra-ocular device 500 embedded within a polymeric material 505. FIG. 5F shows, in cross-section, intra-ocular device 500 embedded within the polymeric material 505, disposed within a lens capsule 550 of an eye. The polymeric material 505 is configured to couple at least an accommodation sensor of the intra-ocular device 500 to the lens capsule 550 such that accommodation forces applied by the lens capsule are coupled to the accommodation sensor and/or other elements of the intra-ocular device 500. Applied accommodation forces could change an optical power of the polymeric material 505 and/or the intra-ocular device 500 by changing a geometry (e.g., deforming) of the polymeric material 505 and/or the intra-ocular device 500 (e.g., a geometry of the electronic lens 520, additional lenses 527, 529, substrate material 510). Additionally or alternatively, the accommodation force could be detected by an accommodation sensor of the intra-ocular device 500 and the optical power of the electronic lens 520 could be controlled based on the detected accommodation force.

The polymeric material 505 could be composed of one or more of a variety of materials. The polymeric material 505 could include a silicone hydrogel. One or more properties of the contents of the polymeric material 505 (e.g., a ratio of monomers or other chemicals used to form the polymeric material 505) could be specified such that a refractive index or other properties of the polymeric material 505 (e.g., a stiffness) are specified according to an application. In some examples, the polymeric material 505 could be formed within the lens capsule 550, e.g., by injection of a fluid and subsequent solidification of the fluid (e.g., by ultraviolet photopolymerization) into the polymeric material 505.

Coupling of accommodation forces from the polymeric material 505 into the intra-ocular device 500 could be facilitated by one or more haptics 515 formed into the substrate material 510 or otherwise made a part of the intra-ocular device 500. Such haptic could include extended elements and/or holes, as illustrated in FIGS. 5A, 5B, and 5D, or could take other forms according to an application.

V. EXAMPLE METHODS

Figure 6:
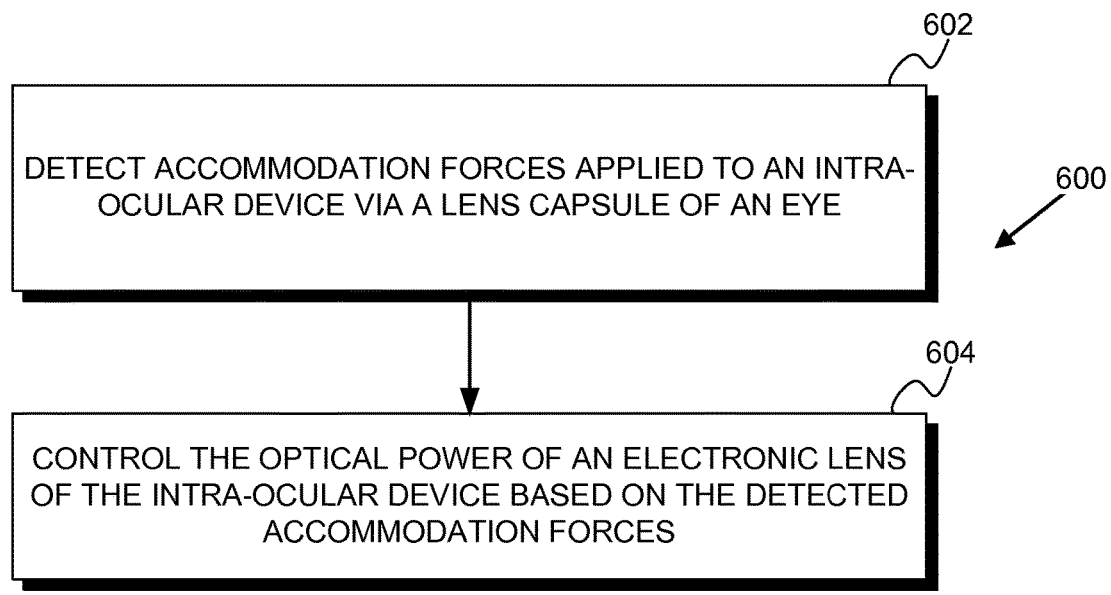
FIG. 6 is a flowchart of an example process.

FIG. 6 is a flowchart of a method 600 for operating an intra-ocular device to control an overall optical power of the intra-ocular device based on a measured accommodation force applied to the intra-ocular device via a lens capsule of an eye. The intra-ocular device includes (i) an electronic lens having an optical power that can be controlled within a range of optical powers and whose optical power is controlled in part by an electrical signal applied to the electronic lens, (ii) an accommodation sensor configured to detect accommodation forces applied to the intra-ocular device via the lens capsule of the eye, and (iii) a controller operatively coupled to the electronic lens and the accommodation sensor and configured to apply an electronic signal to the electronic lens to control the optical power of the electronic lens based on the accommodation forces detected using the accommodation sensor. The intra-ocular device and elements thereof could be configured and/or operated as described herein. Further, the intra-ocular device could include additional components configured to provide some functionality. For example, the intra-ocular device could include a polymeric material that contains the electronic lens, accommodation sensor, and controller and that is configured to form a coupling between the lens capsule and the accommodation sensor and/or electronic lens, or some other components or combinations thereof.

The method 600 includes detecting accommodation forces applied to the intra-ocular device via the lens capsule of the eye (602) using the accommodation sensor. This could include measuring one or more properties of the accommodation sensor (e.g., a resistance, a capacitance, a voltage, an impedance, a breakdown voltage). Measuring the one or more properties of the accommodation sensor could include applying a specified current, voltage, electrical signal or waveform, or some other electrical stimulus to the accommodation sensor and measuring the response (e.g., a voltage, a current) of the accommodation sensor to the applied electrical stimulus. Detecting accommodation forces applied to the intra-ocular device via the lens capsule of the eye (602) could include performing some determination based on a measured property of the accommodation sensor (e.g., determining a value of an applied force based on a detected voltage, resistance, impedance, or other property of the accommodation sensor).

The method 600 further includes controlling the optical power of the electronic lens of the intra-ocular device based on the detected accommodation forces (604). In some examples, this could include applying an electrical signal having one or more properties determined based on the detected accommodation forces to the electronic lens. One or more properties of the electrical signal could be determined based on the detected accommodation forces using stored calibration data (e.g., stored in the data storage 454). Such calibration data could include one or more values specifying a linear or nonlinear relationship between detected accommodation forces and properties of the electrical signal (e.g., a slope and an offset of a linear relationship, two or more parameters describing a polynomial of a nonlinear relationship). Such calibration data could include a lookup table specifying a plurality of properties of the electrical signal corresponding to a respectively plurality of detected accommodation force levels and/or ranges of levels. One or more properties of the electrical signal determined based on the detected accommodation forces could include an amplitude, a mean value, a frequency, a duty cycle, a waveform, or some other property or properties of the electrical signal.

The method 600 could include additional steps or elements in addition to those depicted in FIG. 6 (i.e., 602, 604). For example, the method 600 could include updating the stored calibration data. Such updating could be performed based on information received from an interface device or form some other device using an antenna, a light sensor, or some other element(s) of the intra-ocular device configured to act as part of a communications channel, or according to some other method. Additionally or alternatively, the intra-ocular device could determine updated calibration data through some other means (e.g., based on recorded detected accommodation forces and/or corresponding electrical signals applied to the electronic lens). In some examples, updated calibration data could be determined based on user indications (e.g., using user controls of an interface device) that an optical power of the electronic lens should be increased. Additionally or alternatively, detected accommodation forces and corresponding controlled properties of the lens-controlling electrical signal could be recorded and used to update the calibration data automatically. For example, the calibration data could be updated such that less accommodative 'effort' (i.e., a smaller applied accommodation force) is required to cause the electronic lens to increase/decrease its optical power by a particular amount.

The method 600 could include transmitting detected values of accommodation forces to an interface device or some other external system and used for some application. In some applications, such transmitted accommodation force information could be used as part of a human interface to a computer, e.g., to determine the distance from the user of an object the user is attempting to focus on. For example, such detected accommodation force information could be used to change a simulated focus and/or depth-of-field of a virtual scene presented to the user. Other additional elements of the method 600 and/or alternative implementations of the listed elements of the method 600 are anticipated.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An intra-ocular device, comprising:
 a polymeric material, wherein the polymeric material is shaped to conform to an inside surface of a lens capsule of an eye at time of implantation, thereby filling the lens capsule with the polymeric material; and
 an active device embedded in the polymeric material, wherein the active device comprises:
  an electronic lens, wherein the electronic lens can be controlled to provide an optical power within a range of optical powers, and wherein the optical power of the electronic lens is controlled in part by an electrical signal applied to the electronic lens;
  an accommodation sensor, wherein the polymeric material forms a coupling between the lens capsule of the eye and the accommodation sensor when the intra-ocular device is disposed in the lens capsule such that the accommodation sensor detects accommodation forces applied by the lens capsule to the accommodation sensor via the polymeric material; and
  a controller, wherein the controller is operatively coupled to the electronic lens and the accommodation sensor, wherein the controller applies the electrical signal to the electronic lens to control the optical power of the electronic lens based on the accommodation forces detected by the accommodation sensor.

2. The intra-ocular device of claim 1, wherein the electronic lens is flexible, wherein the electronic lens comprises a first layer disposed between second and third layers, wherein the first layer comprises a liquid crystal, wherein the second and the third layers comprise flexible conductors that are substantially transparent, wherein a refractive index of the liquid crystal is related to a voltage between the second and the third layers, and wherein applying the electrical signal to the electronic lens comprises applying an oscillating voltage across the second and the third layers.

3. The intra-ocular device of claim 2, wherein at least one of the second or the third layers comprises a plurality of flexible silver nanowires.

4. The intra-ocular device of claim 2, wherein the liquid crystal comprises a nematic liquid crystal.

5. The intra-ocular device of claim 1, wherein the active device further comprises a battery.

6. The intra-ocular device of claim 1, wherein the active device further comprises an antenna.

7. The intra-ocular device of claim 1, wherein the intra-ocular device further comprises an additional lens, wherein the additional lens provides an additional optical power in combination with the optical power of the electronic lens.

8. The intra-ocular device of claim 1, wherein the controller applies the electrical signal to the electronic lens according to calibration data stored in a data storage of the intra-ocular device, wherein the active device further comprises an antenna, and wherein the controller is able to: receive updated calibration data using the antenna; and update the calibration data stored in the data storage based on the received updated calibration data.

9. The intra-ocular device of claim 1, wherein the accommodation sensor comprises a strain sensor.

10. The intra-ocular device of claim 1, wherein the polymeric material comprises a silicone hydrogel.

11. The intra-ocular device of claim 1, wherein the polymeric material is formed by solidifying a fluid injected into the lens capsule of the eye.

* * * * *